United States Patent [19]

Foor et al.

[11] Patent Number: 4,460,689
[45] Date of Patent: Jul. 17, 1984

[54] DNA CLONING VECTOR TG1, DERIVATIVES, AND PROCESSES OF MAKING

[75] Inventors: Forrest Foor, New York, N.Y.; Nancy R. Morin, Cranford, N.J.

[73] Assignee: Merck & Co., Inc., Rahway, N.J.

[21] Appl. No.: 471,394

[22] Filed: Mar. 8, 1983

Related U.S. Application Data

[63] Continuation-in-part of Ser. No. 368,551, Apr. 15, 1982, abandoned.

[51] Int. Cl.³ .................. C12N 15/00; C12N 7/00; C12N 7/02; C12N 1/00; C12N 1/20; C12P 21/00; C12R 1/465

[52] U.S. Cl. .................. 435/172; 435/68; 435/235; 435/239; 435/317; 435/253; 435/886; 935/9; 935/31; 935/23; 935/41; 935/73; 935/75; 935/12

[58] Field of Search ............ 435/317, 172, 235, 239, 435/253

[56] References Cited

U.S. PATENT DOCUMENTS

3,950,357 4/1976 Kahan et al. .................. 435/121

FOREIGN PATENT DOCUMENTS

0020147 5/1980 European Pat. Off. .
0020251 5/1980 European Pat. Off. .
0036259 3/1981 European Pat. Off. .
2018778 4/1979 United Kingdom .
2023612 6/1979 United Kingdom .
2031434 8/1979 United Kingdom .
2046272 4/1980 United Kingdom .
2069503 2/1981 United Kingdom .

OTHER PUBLICATIONS

Stenesh Dictionary of Biochemistry, John Wiley & Sons, p. 78, 1975.
J. E. Suarez and K. F. Chater; 6 Cienc. Biol., pp. 99–110, (1981).
K. F. Chater, C. J. Bruton and J. E. Suarez; 14 Gene, pp. 183–194, (1981).
C. J. Thompson, J. M. Ward and D. A. Hopwood; 286 Nature, pp. 525–527, (1980).
K. F. Chater, C. J. Bruton, W. Springer and J. E. Suarez. 15 Gene, pp. 249–256, (1981).
M. Bibb, J. L. Schottel, and S. N. Cohen; 284 Nature, pp. 526–531, (1980).
J. E. Suarez and K. F. Chater; 286 Nature, pp. 527–529, (1980).
J. L. Schottel, M. Bibb, and S. N. Cohen; 146 Journal of Bacteriology, pp. 360–368, (1981).
K. F. Chater; 21 Developments in Industrial Microbiology, Chapter 6, pp. 65–74, (1980).

*Primary Examiner*—Alvin E. Tanenholtz
*Attorney, Agent, or Firm*—Raymond M. Speer; Hesna J. Pfeiffer

[57] ABSTRACT

Disclosed is the novel bacteriophage TG1, TG1 derivatives, and the corresponding genome or nucleic acid components of such bacteriophages and derivatives of such genome, which are useful as DNA cloning vectors into organisms, such as bacteria, for example, *Streptomyces cattleya* NRRL 8057; portions of such phage genome are additionally useful as adjuncts in recombinant DNA cloning procedures, for example: (1) to permit the maintenance of cloned DNA in the host, either in an integrated state or as an autonomous element; (2) to serve as promoters for increasing expression of endogenous or foreign genes wherein said promoters are ligated to such genes or otherwise serve as promoters; and (3) to serve as regulatory elements for achieving control over endogenous and foreign gene expression; as cloning vectors, TG1, its deletion mutants, and other derivatives serve for the amplification and transfer of DNA sequences (genes) coding for useful functions, for example, genes necessary for the production of the antibiotic thienamycin, or genes necessary for the production of hepatitis B antigen, and of DNA sequences which are useful per se, for example, distinct plasmid vectors which are inherently useful; such modified cloning vectors (hybrid DNA molecules comprising the TG1 genome or portions thereof and foreign DNA sequence) are introduced into the recipient organism by infection, transfection or transformation; wherein the hybrid DNA functions in an integrated mode, in a lytic (vegetative phase) mode and/or in a plasmid mode. Also disclosed are microorganisms comprising TG1 prophage and deletion and hybrid (chimeric) derivatives thereof; and microorganisms comprising hybrid (chimeric) phage-plasmids and derivatives thereof.

26 Claims, 4 Drawing Figures

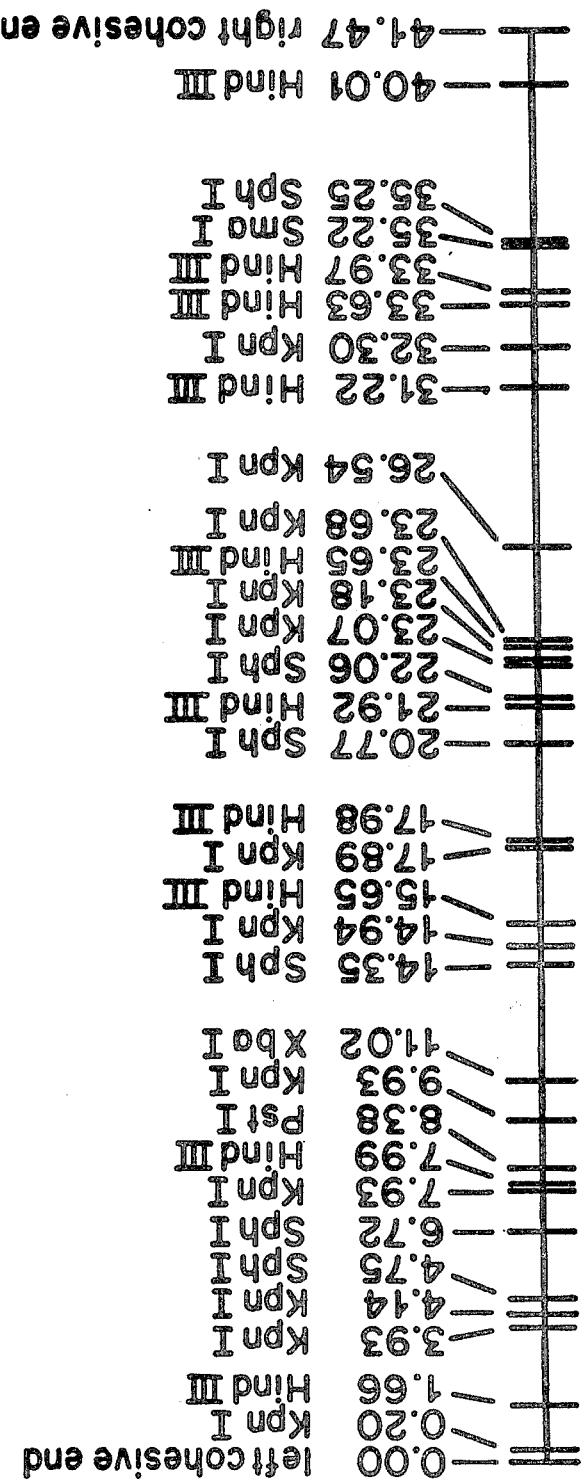
Fig. 2 – Restriction Map of Phage TG1

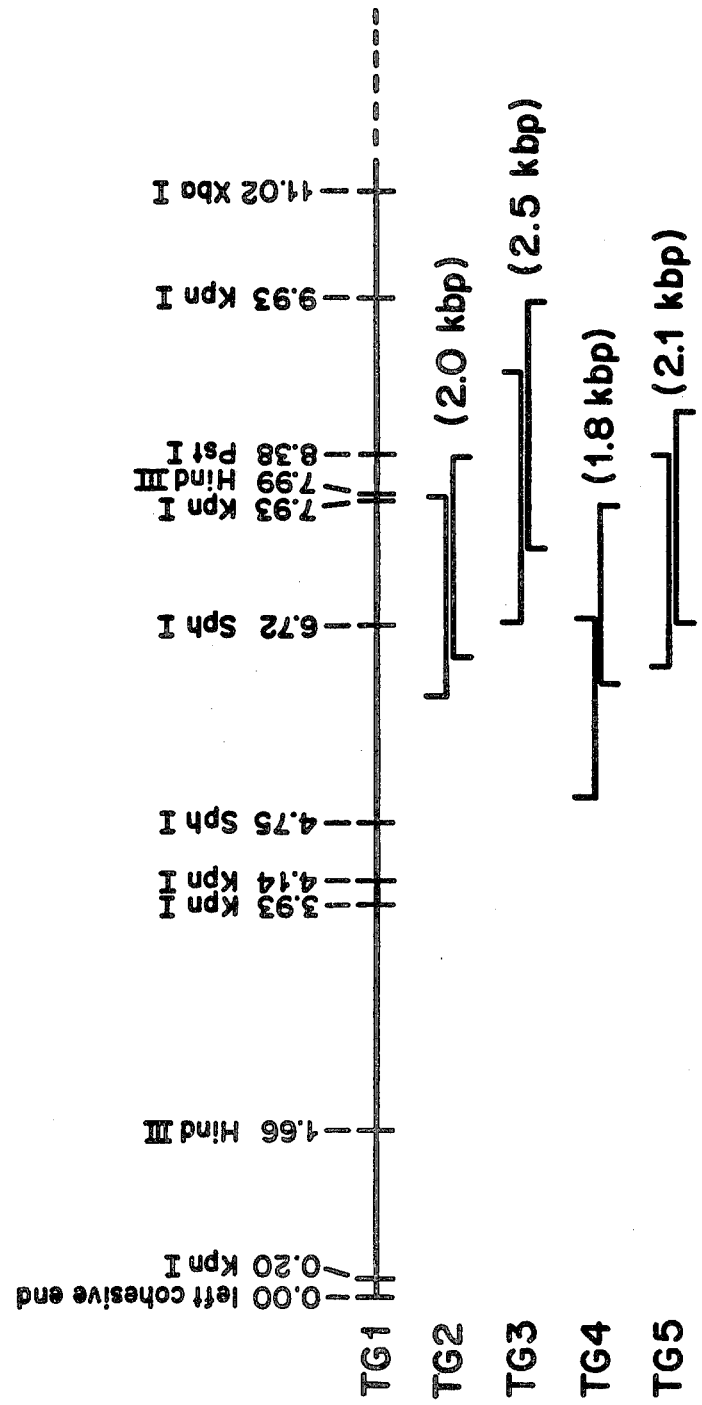
Fig. 3 – Deletion Mutants of Phage TG1

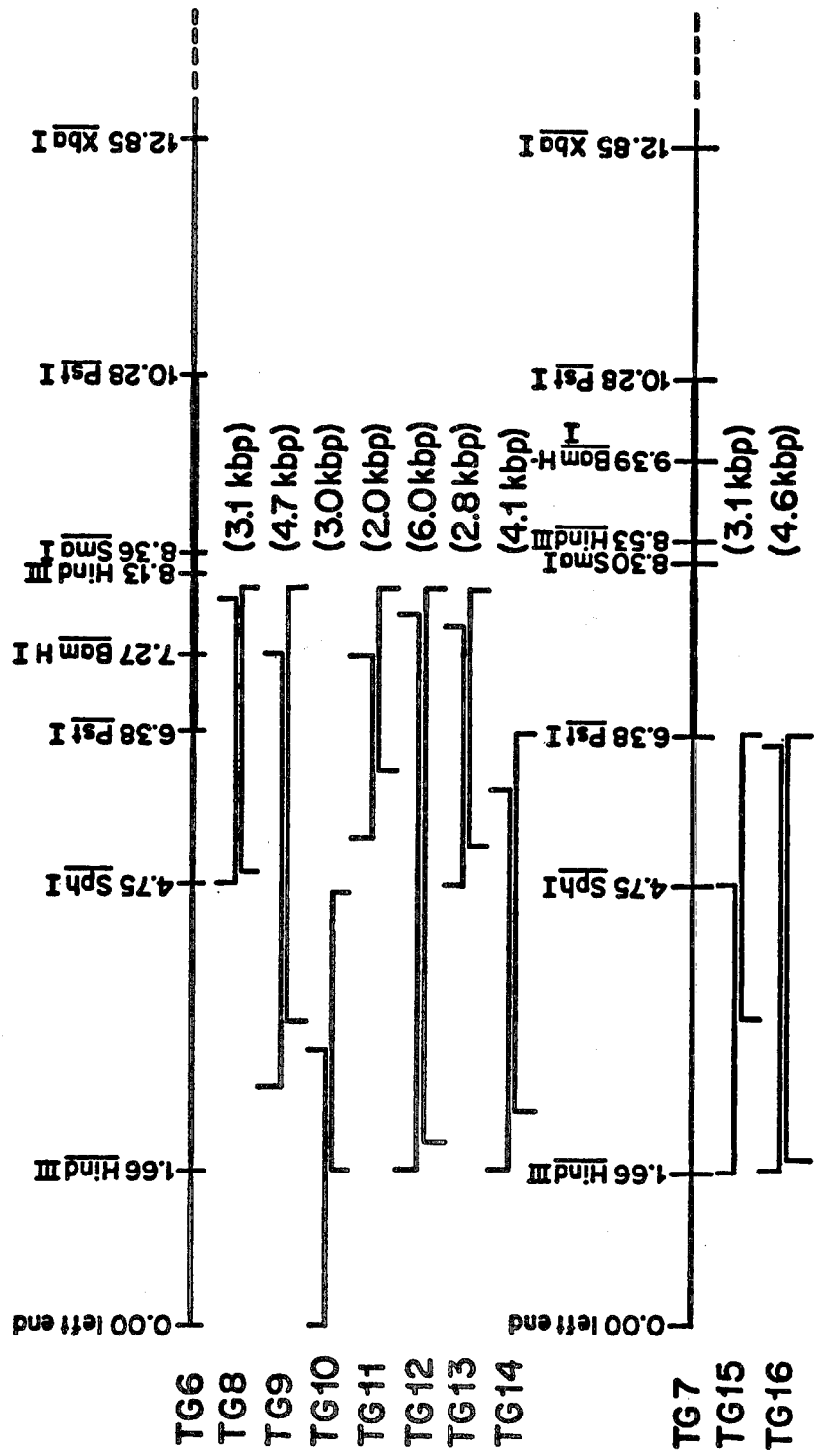

DNA CLONING VECTOR TG1, DERIVATIVES, AND PROCESSES OF MAKING

REFERENCE TO RELATED APPLICATIONS

This is a continuation-in-part of parent application Ser. No. 368,551 filed Apr. 15, 1982 and now abandoned.

BACKGROUND OF THE INVENTION

This invention relates to the incorporation of nucleic acid into cellular systems, to vectors effecting such incorporation, and to microorganisms comprising such vectors.

More specifically, this invention relates to the novel bacteriophage TG1, per se; its genome, or genetic component (DNA), entire and as fragments; and its derivatives (deletion and hybrid variants) thereof which are useful as cloning vectors into organisms, such as bacteria, including in particular phage TG1 host strains, for example, *Streptomyces cattleya* NRRL 8057, *Streptomyces avermitilis* MA4990, *S. viridochromogenes* NRRL 3414, *S. garyphalus* NRRL 2448, or the like. The resultant modified cells are novel and have utility either as a means of producing the foreign nucleic acid and/or its products through replication of the cells and/or induction and replication of the vector as DNA or as phage, or through the imparting of valuable properties to the cells by virtue of the presence of the foreign nucleic acid therein.

The use of bacteriophages for the cloning of DNA is a well-established procedure; however, the application of this technique to phages of the Actinomycetes is recent. In this regard the following articles and patent disclosures are fully incorporated herein by reference:

(1) "Development of a DNA Cloning System in Streptomyces Using Phage Vectors", J. E. Suarez and K. F. Chater; 6 *Cienc. Biol.* pp. 99–110 (1981)

(2) "Restriction Mapping of the DNA of the Streptomyces Temperate Phage φC31 and Its Derivatives", K. F. Chater, C. J. Bruton and J. E. Suarez; 14 *Gene*, pp. 183–194 (1981)

(3) "DNA Cloning in Streptomyces: Resistance Genes from Antibiotic-Producing Species", C. J. Thompson, J. M. Ward, and D. A. Hopwood; 286 *Nature*, pp. 525–527 (1980)

(4) "Dispensable Sequences and Packaging Constraints of DNA from the Streptomyces Temperate Phage φC31", K. F. Chater, C. J. Bruton, W. Springer and J. E. Suarez; 15 *Gene*, pp. 249–256 (1981).

(5) "A DNA Cloning System for Interspecies Gene Transfer in Antibiotic-Producing Streptomyces", M. Bibb, J. L. Schottel, and S. N. Cohen; 284 *Nature*, pp. 526–531 (1980)

(6) "DNA Cloning in Streptomyces: A Bifunctional Replicon Comprising pBR322 Inserted into A Streptomyces Phage", J. E. Suarez and K. F. Chater; 286 *Nature*, pp. 527–529 (1980)

(7) "Cloning and Expression in *Streptomyces lividans* of Antibiotic Resistance Genes Derived from *Escherichia coli*.", J. L. Schottel, M. Bibb, and S. N. Cohen; 146 *Journal of Bacteriology*, pp. 360–368 (1981)

(8) "Actinophage DNA", K. F. Chater; 21 *Developments in Industrial Microbiology*, Chapter 6, pp. 65–74 (1980)

(9) U.K. Patent Application G.B. 2023612A; No. 7919158; published Jan. 3, 1980

(10) U.K. Patent Application G.B. 2031434A; No. 7928156; published Apr. 23, 1980

(11) U.K. Patent Application G.B. 2018778A; No. 7913033; published Oct. 24, 1979

(12) European Patent Application 0036259A2; No. 81 300858.8; published Sept. 23, 1981

(13) U.K. Patent Application G.B. 2046272A; No. 801 1000; published Nov. 12, 1980

(14) U.K. Patent Application G.B. 2069503A; No. 8104473; published Aug. 26, 1981

(15) European Patent Application 0020147A1; No. 8039178.4; published Dec. 16, 1980

(16) European Patent Application 0020251A2; No. 80400722.7; published Dec. 10, 1980.

Based upon extensive characterizing studies, the bacteriophage TG1 of the present invention, isolated from soil, was identified as a hitherto undescribed actinophage. The phage is a temperate, i.e., lysogenic phage of *Streptomyces cattleya* MA4297 (NRRL 8057). The phage has Type B morphology, according to Bradley (David E. Bradley (1967) "Ultrastructure of Bacteriophages and Bacteriocins", *Bacteriol. Rev.* 31, 230–314). The phage head is icosahedral, having a mean head diameter of about 57 nm; the phage tail, including base plate, is about 128 nm in length; as shown by electron microscopy, FIG. 1. The phage nucleic acid is a linear double-stranded DNA molecule 41.47 kilobasepairs in length having cohesive ends. FIG. 2 is a map indicating the locations of the restriction endonuclease cleavage sites of the phage DNA. The locations are given as the distance of the site in kilobasepairs from the end of the phage DNA nearest the single Pst I site. The map shows all sites for the enzymes Hind III, Kpn I, Pst I, Sma I, Sph I, and Xba I which could be determined by agarose gel electrophoresis and ethidium bromide staining of fragments of 0.2 kilobasepairs and larger. The following enzymes fail to cleave the DNA: BamH I, Nae I, Nar I, Pvu II, Sst I, Sst II, Stu I, and Xho I. Certain phage deletion variants and hybrid phage derivatives are similarly described below. Phage TG1 is described in greater detail below; wherein unambiguous characterizing information relating to isolation, maintenance, propagation of the phage and its nucleic acid, as defined, inter alia, by size and restriction mapping is given. Further, as described below, microorganisms containing TG1 prophage, representative TG1 prophage derivatives and TG1 plasmid derivatives are deposited in a culture collection authorized under the Budapest Treaty on the International Recognition of the Deposit of Microorganisms for the Purposes of Patent Procedure (see Table I).

As disclosed herein, phage TG1, its genome, derivatives, and chimeric DNA molecules comprising TG1 genome, or portions thereof, have utility, inter alia, as cloning vehicles in recombinant DNA procedures.

Phage TG1 has certain properties which make it particularly useful as a DNA cloning vector. Its DNA and derivatives thereof, are readily isolated and amplified by transfection of protoplasts, followed by the lytic growth of the resulting phages (see Example 1, Section J). Deletion mutants retaining these functions, as well as the ability to lysogenize the host, and allowing sufficient space for the insertion of significant quantities (several kilobasepairs) of foreign DNA are readily obtained. In addition, the phage DNA possesses a single cleavage site for the restriction endonuclease Pst I. This site is in a dispensable region of the phage genome. Insertion of foreign DNA at this site does not disrupt the lytic and lysogenic functions of the phage (see Example 1, Sections I and M). Such a unique site suitable for the insertion of DNA is an important feature in a cloning vector, since the probability of obtaining hybrid molecules of the required configuration is greatly increased when only two new DNA junctions need to be formed.

A wide choice of restriction enzymes which can be used for cloning into a vector is of great advantage in recombinant DNA experiments. A large number of restriction endonucleases fail to cleave the phage DNA (see above, and Example 1, Section H.) The unique Pst I site can be converted to a unique site for any one of these enzymes by the use of adaptor molecules (see R. J. Rothstein, L. F. Lau, C. P. Bahl, S. A. Narang and R. Wu in Vol. 68 (1979), *Methods in Enzymology*, S. P. Colowick and N. O. Kaplan (Eds.), pp. 98-109). Another technique for the conversion of the Pst I cloning site to a different unique site is the insertion of a short fragment containing the desired site. Example 2, Section A, includes a method for the insertion into the Pst I site of a short fragment with a single BamH I site flanked by Pst I sites.

The ability of the TG1 vector and its derivatives to insert into the host DNA is another important property. It allows the construction and stable integration into the host of hybrid vectors carrying genes and novel combinations of genes, which can lead to production of compounds new to the host (e.g., hepatitis B surface antigen, see Example 2), or increased production of normal cellular products by, for example, increased gene dose. Integration is also useful for the identification of cloned genes by genetic complementation of host mutants. Once the lysogen containing the gene is identified, the vector allows the recovery of the gene in large quantity simply by the propagation of phage obtained from the lysogen, followed by the isolation of the phage DNA. Thus, the vector is useful for the production of large quantities of the DNA of the plasmid pACYC177 (see Example 1, Section M).

The host range of the phage is of particular interest. *Streptomyces cattleya* MA4297 (NRRL 8057) produces the compound thienamycin (see U.S. Patent 3,950,357). Thienamycin has a potent anti-microbial activity against both gram-positive and gram-negative bacteria. It is also effective against bacteria resistant to beta-lactam antibiotics, such as penicillins and cephalosporins, due to the presence of beta-lactamases. Another phage host *Streptomyces avermitilis* produces the complex of chemically related agents called avermectin, which exhibits extraordinarily potent anthelmintic activity (see R. W. Burg et al; 15 *Antimicrobial Agents and Chemotherapy*, pp. 361-367 (1979)). The phage can be used for the identification, isolation, and study of the genes and gene products involved in the synthesis and regulation of the synthesis of these important compounds by genetic complementation of mutations in these genes (e.g., for thienamycin, see Example 3).

Certain hybrid derivatives of phage TG1 are useful in other ways. These hybrids, whose construction and properties are described in Example 1, Section M, allow TG1 vector derivatives to replicate as plasmids in *Escherichia coli*. These hybrid phage-plasmid vectors can be transferred between species by transfection or transformation. This property is extremely useful, since it allows the use of genetic techniques which have been developed for *Escherichia coli*. For example, genes from *S. cattleya* may be found capable of complementing mutations in *E. coli*. Mutations can be introduced into the *S. cattleya* gene in *E. coli*, for instance, by the use of transposon mutagensis; or mutations capable of being suppressed by nonsense suppressors (translational stop codons) might be isolated. The latter mutated genes can be transferred back into *S. cattleya* and used to isolate mutations capable of suppressing translational stop codons in *S. cattleya*. Such suppressor mutations are very useful in genetic studies of such an organism. The ability of the vector to replciate in *E. coli* is also useful in other ways. This property was used for the selection of deletions of vector DNA which were outside the region of the inserted plasmid DNA (see Example 1, Section N). Such deletions are important for the eventual cloning of significant quantities of DNA in the vector.

TG1 and its derivatives can be used in other ways to clone DNA sequences excised using a variety of restriction enzymes appropriate for insertion into the DNA of the particular phage vector. A useful compendium of recombinant DNA techniques is *Methods in Enzymology*, Vol. 68 (1979), Academic Press, New York. Modifications in cloning procedure can include, besides the use of other phage variants and other restriction enzymes: treatment of the restricted vector DNA with phosphatase to remove terminal phosphate groups and thus prevent self ligation of the vector DNA; the use of blunt end ligation following removal of the single stranded ends produced by cleavage with a restriction enzyme with S1 nuclease or synthesis of the complement of such single stranded ends with DNA polymerase; and/or DNA tailing reactions providing cohesive ends between vector and the DNA to be inserted (see Nelson and Brutlag, *Methods in Enzymology*, Vol. 68 (1979) pp. 41-50).

Transfection frequencies may be improved by altering the described conditions or constituents, or by use of liposome encapsulation of ligated DNA followed by fusion of such liposomes to protoplasts of the recipient bacteria. Such a procedure was recently described by J. F. Makins and G. Holt (Nature 293 (1981) pp. 671-673) for liposome transformation of chromosomal DNA. The procedure used may be that described or variations of it.

Screening of phage clones or lysogens for hybrid phage containing the desired inserted DNA may be carried out in several ways depending upon the phenotypic or genotypic nature of the insert. For example, genes capable of complementing mutants blocked in the synthesis of primary metabolites such as inter alia, amino acids, vitamins, purines or pyrimidines can be detected in the following manner. Specific mutant strains are protoplasted and transfected with the ligated DNA and allowed to regenerate in the absence of any selection. The resulting colonies include non-transfected cells, lysogens formed from transfection by non-hybrid phage, as well as those arising from transfection by hybrid phage. Lysogens containing the desired insert are isolated by plating the regenerated culture on minimal media deficient in a particular nutrient. Colonies arise only from those regenerated lysogens that contain the appropriate DNA insert. A second method that also can easily allow for the detection of the desired insert is to transfect wild type protoplasts with ligated DNA, mix these with wild type germlings and plate the mixture on appropriate plates to allow for plaque formation. The developed plates contain plaques due to religation of the parental phage and those due to phage carrying inserts (essentially the same as a method used Phage promotor sequences can also be utilized to place chromosomal genes under different controls. Some of the phage promoters are regulated by phage regulator mechanisms. Thus expression of properly inserted cloned genes will also be controlled by such mechanisms. For example, a temperature sensitive repressor may, at low temperature, greatly lower the expression of a particular promoter by binding to an operator site, at elevated temperature the repressor may be inactive and transcription at high levels may occur. If a desired cloned gene were inserted at an appropriate position, its expression and the level of the gene product could be controlled during a fermentation by adjusting the temperature.

TABLE I

Microorganism Deposit

| Strain Number[a] | Resident Vector | Accession Number[b] |
|---|---|---|
| MA5766 | TG2 | ATCC 39077 |
| MA5767 | TG1 | ATCC 39078 |
| MA5769 | TG4 | NRRL 15034 |
| MA5770 | TG5 | NRRL 15035 |
| MB4540 | pTG6 | ATCC 39079 |
| MB4541 | pTG12 | ATCC 39080 |
| MB4542 | pTG16 | ATCC 39081 |
| MB4543 | pTG7 | ATCC 39082 |
| MB4544 | pTG15 | NRRL B-15027 |
| MB4545 | pTG8 | NRRL B-15028 |
| MB4546 | pTG9 | NRRL B-15029 |
| MB4547 | pTG10 | NRRL B-15030 |
| MB4548 | pTG11 | NRRL B-15031 |
| MB4549 | pTG13 | NRRL B-15032 |
| MB4550 | pTG14 | NRRL B-15033 |

[a]Strain designations are those of the culture collection of MERCK and CO., Inc., Rahway, New Jersey. MA5766–MA5770 are derivatives of *Streptomyces cattleya* MA4297 (NRRL 8057) lysogenic for the indicated phage vectors. MB4540–MB4550 are derivatives of *Escherichia coli* K-12 RR1 containing the indicated hybrid phage-plasmid vectors. *E. coli* K-12 RR1 is described by F. Bolivar, R. L. Rodriquez, M. C. Betlach, and H. W. Boyer; 2 Gene, pp. 75-93 (1977).

[b]Cultures of each strain have been placed on permanent deposit with the American Type Culture Collection (ATCC), 12301 Parklawn Drive, Rockville, Md., and were complete as of April 2, 1982; and at the Agricultural Research Culture Collection (NRRL), Fermentation Laboratory, Northern Regional Research Center, Science and Education Administration, U.S. Department of Agriculture, 1815 North University Street, Peoria, Ill., as of April 2, 1982; and were assigned the indicated accession numbers.

LEGENDS TO THE FIGURES

FIG. 1: Electron micrograph of phage TG1. The sample was stained with 2% phosphotungstic acid aqueous (pH 6.3, adjusted with 1.0M KOH). The specimen was examined at a magnification of 210,570 in a Philips 300 Transmission Electron Microscope.

FIG. 2: Restriction map of phage TG1. The locations are given as the distance of the site in kilobasepairs from the end of the phage DNA nearest the single Pst I site, which is arbitrarily designated as the left end. The map shows all sites for the enzymes Hind III, Kpn I, Pst I, Sma I, Sph I, and Xba I which could be determined by agarose gel electrophoresis and ethidium bromide staining of fragments of 0.2 Kilobasepairs and larger.

FIG. 3: Deletion mutants of phage TG1. The deletions were analyzed by digestion of the DNA with the enzymes Hind III, Kpn I, Pst I, Sph I, and Xba I. The locations of restriction sites for TG1 are given, as in FIG. 2, in kilobasepairs from the left end of the phage DNA. The uncertainty in the location of deleted DNA for each derivative is indicated by horizontal brackets drawn below the map of TG1. Note that only the left end of the phage map is shown. No deletions occurred outside of this region. The left most possible location of a deletion is indicated by an upward-facing bracket, while the rightmost possible location is indicated by a downward-facing bracket. The length of each deletion in kilobasepairs (kbp) is given in parenthesis to the right of the relevant brackets, while the phage mutant is identified on the left. Note that if a site at the end of one bracket is missing in the mutant, it is occluded by the other bracket; otherwise, the site is present.

FIG. 4: Hybrid phages TG6 and TG7 and deletion mutants. Note that only the left ends of the restriction maps of TG6 and TG7 are shown. All restriction sites to the right of the Pst I site at 10.28 kbp are identical to those of TG1 as shown in FIG. 2, except that the locations of the restriction sites must be increased by the addition of 1.9 kbp to take into account the deletion of 2.0 kbp of DNA just to the left of the Pst I site (see TG2 in FIG. 3) and the insertion of 3.9 kbp of pACYC177 DNA into this site. The region comprising DNA from pACYC177 is indicated by the heavy line between the Pst I sites at 6.38 kbp and 10.8 kbp. The deletions in the various derivatives are indicated below the relevant parent in the same manner as for FIG. 3.

Thus, it is an object of the present invention to provide the novel bacteriophage TG1 per se, and derivatives thereof; the genome (nucleic acid) component of such phages, and derivatives thereof, including deletion mutants, hybrid (chimeric) nucleic acid molecules comprising phage TG1 genome or portions thereof and other DNA sequences, which are useful as DNA cloning vectors into organisms, such as bacteria, for example, *S. cattleya* NRRL 8057; portions of such phage genome are additionally useful as adjuncts in recombinant DNA cloning procedures, for example; (1) to permit the maintenance of cloned DNA in the host, either in an integrated state or as an autonomous element; (2) to serve as promoters for increasing expression of endogenous or foreign genes wherein said promoters are ligated to such genes or otherwise serve as promoters; and (3) to serve as regulatory elements for achieving control over endogenous and foreign gene expression; as cloning vectors, TG1 and its deletion mutants serve as carriers of DNA sequences (genes) coding for useful functions, for example, genes necessary for the production of the antibiotic thienamycin, or genes necessary for the production of hepatitis B antigen, and of DNA sequences which are useful per se, for example, distinct plasmid vectors which are inherently useful; such modified cloning vectors (hybrid DNA molecules comprising the TG1 genome or portions thereof and foreign DNA sequence) are introduced into the recipient organism by infection, transfection or transformation; wherein the hybrid DNA functions in an integrated mode, in a lytic (vegetative phase) mode and/or in a plasmid mode. Thus, an additional object is to provide microorganisms comprising TG1 prophage and deletion and hybrid (chimeric) derivatives thereof; and microorganisms comprising hybrid (chimeric) phage-plasmids and derivatives thereof. (The term "TG1 vector", used in the generic sense, comprises the bacteriophage which is TG1 and all its derivatives; the genome, entire and portions thereof, of TG1 and its derivatives; and cloning vectors comprising the genome, entire and portions thereof, of TG1 and its derivatives.)

DETAILED DESCRIPTION OF THE INVENTION

Figure 1:
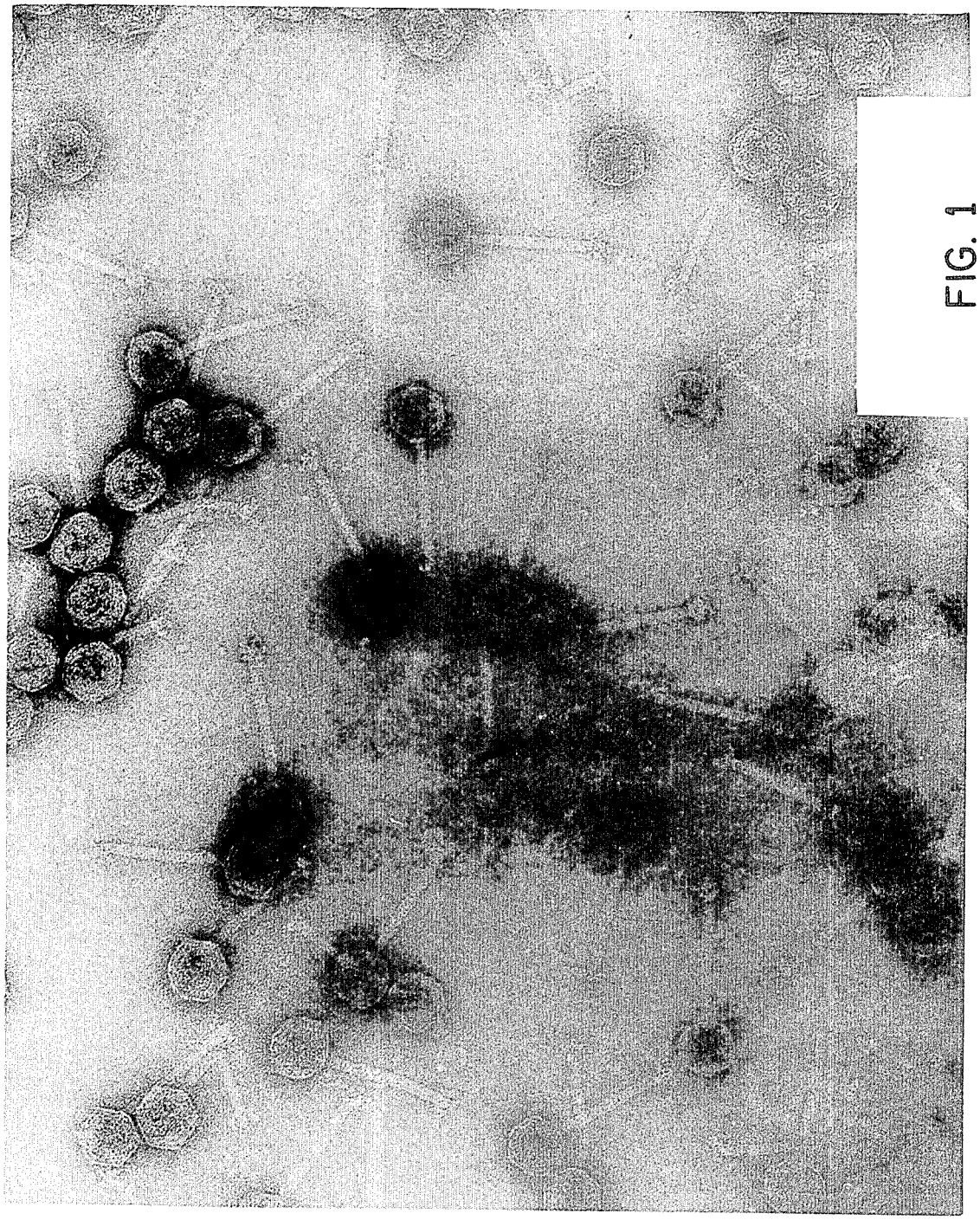

The invention in several of its embodiments is representatively disclosed in this section in the format of "Examples". It is to be understood that this format is for isolating the insertion of plasmid pACYC177 into a TG1 derivative, (See Example 1, Section M). The phage are harvested and a sterile phage stock obtained as described in Example 1, Section B. These lysates are used for a transduction of appropriate mutant strains. Only the phage containing the desired insert are capable of transducing the particular mutation and allow for the formation of a colony.

In the case of mutants blocked in the production of a secondary metabolite, such as an antibiotic, which does not normally have an easily detectable growth phenotype, the phage containing the desired insert are detected by plating lysogens obtained by either of the above described methods on appropriate plates. After allowing a period of time for colonies to develop, the plates are flooded with a culture of an organism sensitive to the antibiotic and further incubated. Lysogens containing an insert with a functioning antibiotic synthetic gene produce the antibiotic and cause the formation of a zone of growth inhibition surrounding the colony (see Example 2).

Phage containing inserts of DNA that do not confer any detectable phenotype, such as ribosomal RNA or transfer RNA, can be detected by either plaque of colony hybridization using complementary DNA as probes.

The efficiency of isolating desired clones can be significantly increased if a method for the direct selection of lysogens is developed. Such a selection can be accomplished using as a vector phage DNA that contains an insert of DNA coding for resistance to an antibiotic (see Examples 2 and 3) or a biosynthetic step. Either selection would eliminate from the analysis, colonies arising from uninfected protoplasts.

Phage clones containing genes for antibiotic synthesis can be used for several other experiments. The phage can be used to transduce wild type, or other antibiotic producing cultures to examine the effect of increased dosage of the particular cloned gene on production levels. The techniques of localized mutagenesis may be employed to isolate mutations in the specific cloned gene thus eliminating the introduction of distant but possibly deleterious lesions into a strain. Such localized mutagenesis will likely result in the isolation of mutations increasing or decreasing the production of antibiotic, and will aid in the improvement of producing cultures and in the genetic analysis of antibiotic synthesis and regulation. Recombinant DNA techniques may also allow for the introduction of high level promotor sequences at an appropriate site to greatly increase the expression of the particular antibiotic synthetic gene. The increased amount of gene product may signficantly increase the productivity of the strain. The cloned gene product may be identified by infection of UV irradiated host cells, followed by infection with the particular hybrid phage. Growth in the presence of radio-labelled amino acids would result in the synthesis of radio-labelled proteins coded for by the phage. Proteins coded for by the host cell would not be synthesized due to the damage caused by the UV treatment. The proteins can be separated and analyzed by standard techniques.

Foreign DNA, that is, DNA from sources other than the host organism, can also be inserted into the phage vector. The insertion of pACYC177 into the phage is one example of this. In such cases the presence of a host restriction system may greatly lower the frequency of transfection and thus make detection of desired clones difficult. Bacterial mutants defective in host restriction may be isolated to eliminate this problem. Such a strain and its derivatives can then serve as the host for cloning experiments. Examples of foreign DNA that may prove to be useful include, antibiotic resistance genes, genes coding for informational suppressors (transfer RNA), or mutagenic elements such as transposons or mutator genes.

Cloned antibiotic genes may be physically isolated using standard recombinant DNA techniques and transferred to other cloning vectors. These may include plasmids that replicate in the host organism or those that replicate in other strains. Cloned antibiotic genes may be tranferred via TG1 or its derivatives to other Streptomyces strains that normally do not produce the antibiotic. This transfer may result in the synthesis of new antibiotics, or altered expression of the cloned gene.

The vectors can be used in several other ways to achieve DNA cloning. Normally a plasmid of an unrelated bacterial strain, for instance a plasmid of *E. coli*, if introduced into a phage host strain, will not replicate or be maintained because of its foreign origin. If, however, the plasmid has been altered by the insertion of a DNA sequence homologous to one present in the host chromosome, a recombination event can result in the integration of the plasmid into the chromosome at the site of homology. If the host strain is a phage lysogen, the homologous sequence on the plasmid can be provided by a phage fragment. In this case the plasmid will insert into the prophage which is integrated in the chromosome. Such an inserted plasmid will be maintained as a part of the host chromosome as long as the prophage remains integrated. Alternatively, a specific phage fragment carrying functions necessary for the normal integration of the phage, that is, the attachment site and phage genes coding for gene products necessary for phage integration, can be inserted into the plasmid. Such a vector should be capable of integrating into the host chromosome at the same site as, and in a manner analogous to, the integration of the wild type phage. Recombinant bacteria carrying the inserted vectors can be easily identified if a selectable genotype is also carried by the vector. Vectors of this type have several important advantages: (1) the amount of DNA which can be cloned into such a molecule is not limited by phage packaging constraints; (2) the plasmid can replicate in its orginial host, for instance *E. coli*, where various genetic and physical manipulations may be easier to achieve than in the Streptomyces host; (3) an element, such as the lambda cos site can be introduced, allowing cloning of large DNA fragments by the technique of cosmid DNA cloning (see *Methods in Enzymology*, Vol. 68) in the plasmid host, e.g., *E. coli*, followed by isolation of the resulting hybrid DNA and transformation or transfection of protoplasts of the Streptomyces strain.

Other phage sequences may also be used for cloning purposes. One such sequence is the cos site of phage TG1. This site is recognized by a phage product during packaging of DNA into phage capsids. A minimal length of DNA is required between successive cos sites for efficient packaging. If the cos site is inserted into a plasmid and other DNA is also inserted then an in vitro packaging system can be used to process the DNA and form phage particles. Only those inserts that create the correct length of DNA between cos sites can be packaged and thus large inserts are selected.

merely chosen as a convenient form of disclosure, without imposing any limitation upon the invention as hereinabove disclosed.

EXAMPLE 1

Isolation, Construction, Maintenance, and Propagation of TG1 Vectors

The phage and DNA were isolated and handled by procedures differing little from those established by work on other bacteriophages and plasmids used as cloning vectors. A good procedures manual is R. W. Davis, D. Botstein, and J. R. Roth, "A Manual for Genetic Engineering: Advanced Bacterial Genetics," Cold Spring Harbor Laboratory, Cold Spring Harbor, N.Y. (1980). The specific procedures used in this work are described herein, unless they are identical to those given in the above mentioned manual. Results which serve to characterize the TG1 vector and its derivatives and differentiate them from other cloning vectors are mentioned where appropriate.

A. Isolation of Phage TG1

Approximately 300 diverse soil samples were examined for the presence of phage capable of growing on *S. cattleya*. Soil samples were tested for the presence of phage by mixing 1 gram of soil with 5 ml of YC broth containing germlings at a concentration of $10^5$ per ml and incubating 16 hours with shaking at 30° C. Germlings are prepared by incubating spores of *Streptomyces cattleya* MA4297 at a concentration of $10^7$ colony-forming units (cfu) per ml at 37° C. for 3 hr in YC broth with shaking. YC broth contains 4.0 g Difco yeast extract, 10 g Difco malt extract, and 4.0 g D-glucose per liter; ten ml each of 1.0M $MgCl_2$ and 2.5M $CaCl_2$ are added per liter after autoclaving. The broth which had been incubated with the soil was filtered, a drop was spotted on a plate overlaid with soft agar containing $10^6$ germlings, and the plate was incubated 16 hours at 30° C. The overlay was prepared by mixing 0.1 ml of germlings with 4.0 ml of YC soft agar and pouring into a petri plate containing about 40 ml of YC agar. YC soft agar is YC broth containing 0.6% (w/v) of molten Difco agar at 46° C. YC agar is YC broth solidified with 2.0% (w/v) Difco agar.

The soft agar was removed from zones of bacterial lysis, and the putative phage extracted and diluted with YC. A sample of 0.1 ml of each dilution was mixed with 0.1 ml of germlings. After 10 to 20 min at room temperature 4.0 ml of YC soft agar was added. This mixture was poured into a petri plate containing 40 ml YC agar. After the soft agar overlay had hardened, the plates were incubated 16 hours at 30° C. Small zones of bacterial lysis, called plaques, formed from the growth and multiplication of a single phage, were observed on plates to which only a few phage were added. The number of plaques observed on each plate is directly proportional to the concentration of phage in the suspension. Approximately 30 different phage isolates were obtained. Phage TG1 was unusual in that zones of confluent lysis became turbid after two further days of incubation. This observation suggested that the phage was temperate, i.e., lysogenic. This possibility was investigated in detail (see Sections C and E below).

B. Growth of Phage TG1

Phage TG1 grows best between 28°–32° C. $Ca^{++}$ is required for the formation of plaques. Plaques are typically 1 to 3 mm in diameter. Divalent cations ($Mg^{++}$ is sufficient) are required for stability, as evidenced by the inactivation of the phage in the presence of chelating agents, such as, pyrophosphate and ethylenediaminetetraacetate (see Sections I and N below).

To propagate the progeny of a single phage the soft agar from the center of a plaque is removed and mixed with 10 ml YC broth containing germlings at $2 \times 10^7$ cfu per ml and incubated 16 hours at 30° C. in a $25 \times 150$ mm culture tube in a tissue culture roller drum (New Brunswich Scientific, Model TC-7) rotating at a rate of 40 to 50 r.p.m. The resulting lysate is passed through a filter with a pore size of 0.45 micron. The filtrate constitutes a phage tube stock and typically contains $10^{10}$ pfu per ml.

The agar overlay from a plate infected with enough phage to give confluent lysis, about $10^4$ plaque-forming units (pfu), can be removed and resuspended with 5.0 ml YC broth. This mixture is mixed vigorously for about ten sec. The agar is removed by centrifugation, and the supernatant fluid is filtered. The filtrate constitutes a phage plate stock and typically contains $10^9$ pfu per ml. Phage stocks are stored at 4° C.

C. Isolation and Demonstration of Lysogens

If plates with plaques are incubated one or two additional days, a small amount of bacterial growth can usually be observed within the zone of lysis. These bacteria are removed and sporulated. The spores are washed free of contaminating phage, diluted, and grown as isolated colonies. Spores or vegetative cells from such purified cultures are lysogenic if upon further growth some of the cells release phage, and the culture fluid accumulates new free phage which can be separated from the bacteria by filtration, and the cells themselves are resistant to lysis from infection with free phage.

A phage preparation from a tube of lyophilized spores of a *Streptomyces cattleya* phage lysogen is obtained in the following manner. A tube of lyophilized spores is opened aseptically, and the contents suspended in 10 ml of sterile YC broth contained in a $25 \times 150$ mm culture tube and incubated 6 hours at 30° C. in a tissue culture roller drum rotating at a rate of 40 to 50 r.p.m. The culture fluid is passed through a filter with a pore size of 0.45 micron. The phage in the resulting suspension can be maintained and propagated as described above.

D. Isolation of Chromosomal DNA from Streptomyces cattleya

Approximately $10^7$ spores are used to inoculate a 250 ml baffled Erlenmeyer flask containing 25 ml of YC broth without the divalent cation additions but with 0.1% (w/v) glycine. The flask is shaken on a 220 r.p.m. shaker (2 inch throw) at 37° C. for 16 hours at which time the growth is satisfactory. The cells are collected by centrifugation, washed once with 25 ml of 0.09% (w/v) NaCl, and resuspended with 5 ml of a solution containing 25% (w/v) sucrose and 50 mM tris(hydroxymethyl)aminomethane which has been adjusted to pH 8.0 with hydrochloric acid and to which hen egg white lysozyme has been added to a final concentration of 2 mg per ml just before use. This mixture is incubated for 1 hour at 37° C., then combined with 2.5 ml of a solution containing 0.25M disodium ethylenediaminetetraacetate which has been adjusted to pH 8 with NaOH. The mixture is incubated 15 min. on ice and combined with 7.5 ml of a solution containing 2.0% (w/v) N-lauroyl-N-methylglycine. After an additional 30 min. on ice, bovine pancreatic ribonuclease A is added (0.15 ml of a 5 mg per ml solution in 0.1M Na acetate, which has been heated for 10 min. at 100° C.), followed by Pronase® (0.6 ml of a freshly prepared solution, which has been incubated for 45 min. at 37° C. just before use, containing 25 mg per ml of Pronase® dissolved in buffer P; buffer P contains 50 mM NaCl, 5 mM disodium ethylenediaminetetraacetate, and 30 mM tris(hydroxymethyl)aminomethane which has been adjusted to pH 7.5 with hydrochloric acid). The resulting mixture is incubated for 2 hours at 37° C. This lysate is extracted three times for 30 min. with an equal vol. of phenol, which has been neutralized just before use by equilibrating three times with an equal volume of a solution containing 0.2M tris(hydroxymethyl)aminomethane which has been adjusted to pH 7.9 with hydrochloric acid. The lysate is next extracted ten times with an equal vol. of chloroform and then mixed with a tenth vol. of acetate solution (containing 3.0M Na acetate and 1.0 mM disodium ethylenediaminetetraacetate, which has been adjusted to pH 7.0 with NaOH), after which 0.54 vol. isopropanol is added. The DNA is recovered by spooling on a glass rod and redissolved with 5.0 ml water containing 0.1% (v/v) diethylpyrocarbonate. It is precipitated two more times in succession in a similar manner, except that it is redissolved, after each subsequent precipitation, with 5.0 ml of a solution containing 10 mM tris(hydroxymethyl)aminomethane and 1.0 mM disodium ethylenediaminetetraacetate which has been adjusted to pH 8.2 with hydrochloric acid.

E. Gel Transfer Hybridization Analysis of Phage TG1 Lysogen DNA

DNA digested with the appropriate restriction enzymes is fractionated by agarose gel electrophoresis. The fragments are depurinated, denatured and transferred to nitrocellulose paper. (Schleicher and Schuell, BA85); radioactive probe is prepared with DNA from purified phage by nick translation; and the probe is denatured with heat and hybridized to the DNA on the nitrocellulose at 42° C. for 48 hours in the presence of formamide, ficoll, bovine serum albumin, and polyvinyl pyrrolidone and in the absence of dextran sulfate, essentially as described by Davis et al., supra.

The phage restriction map was useful for determining the mode of lysogeny of phage TG1. In general, temperature phages lysogenize either as plasmids or by integration into the host chromosome (see Campbell, A. M.: The episomes. Adv. Genet. 11 (1962) 101–145). Knowledge of the mode of lysogenization is of some interest, if the phage is to be used as a DNA vector. These possibilities can be distinguished by gel transfer analysis of lysogen chromosomal DNA digested with the appropriate restriction endonucleases. If the phage lysogenizes as a plasmid, the only difference between prophage DNA and vegetative phage DNA is that the cohesive ends are joined together in the prophage. If the phage integrates, however, the particular restriction fragment in which the site of integration is located is missing. It is replaced by two new fragments resulting fromn the fusion of the two halves of the original fragment with chromosomal DNA. Our results indicate that phage TG1 integrates into the chromosome of *S. cattleya*. The enzymes Pst I and Cla I were chosen, so that the phage DNA was split into essentially two regions: a large internal fragment of 25 kbp, and a fragment 16.3 kbp in size, called the cos fragment, which results from the joining together of two fragments having the phage cohesive ends. The latter two fragments are 8.4 and 7.9 kbp in size. DNA from the vegetative phage (0.01 μg) and chromosomal DNA from a lysogen (1.0 μg) were digested with these enzymes and fractionated on an agarose gel. The restriction pattern was analyzed by hybridization with radioactively labelled phage DNA as described above. DNA from a nonlysogen contained no sequences homologous to the phage DNA. The cos fragment was missing in the lysogen and was replaced by two new fragments hybridizing with phage DNA, which were 15 and 11 kbp in size. This result showed that the phage DNA integrated into the host DNA.

F. Purification of Phage Particles

A 1.0 ml sample of a phage plate stock or a phage tube stock is added to 1.0 liter of YC broth at 30° C. containing germlings at $10^7$ cfu per ml. The culture is incubated in a 2.0 liter flask on a rotary shaker (2 inch throw) at 220 rpm 16 hours at 30° C. The lysate is clarified by filtration through glass wool and contains about $10^9$ pfu per ml. The phage is precipitated by the addition of 20 g NaCl and 100 g polyethylene glycol (average mol. wt. 6,000). After dissolution of the additions with stirring, the mixture is allowed to sit overnight at 4° C. without stirring. The phage is sedimented by low speed centrifugation. The pelleted material is resuspended with 10 ml SM buffer. SM buffer contains 0.5% (w/v) NaCl, 20 mM tris(hydroxymethyl)aminomethane, 0.01% gelatin, 10 mM $MgCl_2$, and 5 mM $CaCl_2$, the whole adjusted to pH 7.5 with hydrochloric acid.

The suspension is clarified by centrifugation at $2500 \times g$ for 5 min. The supernatant fluid is placed in a fresh centrifuge tube and underlayered with 2.0 ml of a solution of CsCl in SM buffer with enough CsCl to give a density of 1.3 g per ml, 2.0 ml with a density of 1.5 g per ml, and 2.0 ml with a density of 1.7 g per ml. The tube is centrifuged for 1.5 hr at 50,000 rpm in a Beckman 60 Ti rotor at 10° C. (average r.c.f., $180,000 \times g$). The phage particles are visible as a turbid band at the interface of the bottom two layers. The material in this band is removed with a pipet, mixed with enough additional CsCl in SM buffer with a density of 1.5 g per ml to give a final volume of 10 ml, and centrifuged for 16 hr in a Beckman 80 Ti rotor at 40,000 rpm at 10° C. (average r.c.f., $110,000 \times g$). The phage are again visible as a turbid band near the middle of the tube and are removed with a pipet. This phage suspension is dialyzed successively against 2.0 liter batches of buffer containing, respectively 1.0M, 0.3M, 0.1M, and 0.01M NaCl dissolved in a solution containing 20 mM tris(hydroxymethyl)aminomethane, 10 mM $MgCl_2$, and 5 mM $CaCl_2$ which has been adjusted to pH 7.5 with hydrochloric acid.

G. Preparation of Phage DNA

The DNA can be prepared from purified phage particles by standard procedures, two of which are outlined here.

Procedure 1. Redistilled phenol is equilibrated with 1.0 vol. of 0.2M tris(hydroxymethyl)aminomethane adjusted to pH 8 with hydrochloric acid, three times in succession. An equal volume of equilibrated phenol is added to a phage suspension and the two phases are mixed for thirty minutes by inverting the tube repeatedly. The phenol (bottom phase) is removed with a pipet. The extraction with phenol is repeated two times. The aqueous phase is extracted with an equal volume of ether three times. The ether which cannot be removed with a pipet is allowed to evaporate. A tenth volume of 3.0M sodium acetate adjusted to pH 6.5 with acetic acid is added followed by two volumes 200 proof ethanol. Precipitated DNA is visible after mixing the ethanol with the aqueous phase. The DNA is recovered by centrifugation for 10 min at 13,000×g. The supernatant fluid is decanted, the pellet washed with 70% (v/v) ethanol, and residual liquid evaporated with a stream of nitrogen gas. The DNA is redissolved with a small volume of TE. TE contains 10 mM tris(hydroxymethyl) aminomethane and 1.0 mM disodium ethylenediaminetetraacetate, and is adjusted to pH 7.8 with hydrochloric acid. Purified DNA is stored at 4° C. or −70° C.

Procedure 2. One fifth volume of a solution containing 0.5M tris(hydroxymethyl)aminomethane and 0.25M disodium ethylenediaminetetraacetate and adjusted to pH 8.0 with hydrochloric acid is mixed with the phage suspension. One five-hundredth volume of diethylpyrocarbonate is added. The mixture is incubated at 37° C. for one hour.

An equal volume of formamide is added. The turbidity due to intact phage particles disappears at this point, and the solution becomes viscous due to the release of DNA. If the CsCl has not been removed from the phage suspension by dialysis, a volume of water equal to the original aqueous volume is added to the formamide containing mixture. Two volumes of 200 proof ethanol are mixed with this solution to precipitate the DNA. The precipitated DNA is recovered and stored as described for procedure 1.

Less pure phage DNA which can nevertheless be used for restriction analysis (see Section H), transfection (see Section J), or transformation (see Section K) can also be prepared by this procedure from phage harvested from a tube lysate by centrifugation for 3 hrs. in a Beckman 80 Ti rotor at 45,000 rpm (average r.c.f., 150,000×g). The phage pellet is resuspended with 0.5 ml of a solution containing 0.2M tris(hydroxymethyl)aminomethane and 25 mM ethylenediaminetetraacetate previously adjusted to pH 8.5 with hydrochloric acid. Diethylpyrocarbonate is added directly to this suspension. The DNA, isolated as described above, is heated 10 min. at 72° C. with bovine pancreatic ribonuclease A added to a final concentration of 10 μg/ml, and stored as before.

H. Restriction Analysis of Phage DNA

DNA was restricted by various combinations of restriction endonucleases and the restriction products analyzed by agarose gel electrophoresis essentially as described by Davis et al., supra. The results show that phage TG1 nucleic acid consists of a linear double-stranded DNA molecule 41.47 kilobasepairs (kbp) in length having cohesive ends. The following enzymes fail to cleave the DNA: BamH I, Nae I, Nar I, Pvu I, Sst I, Sst II, Stu I, Xho I. The following enzymes cleave the DNA at multiple sites: Bgl I, BstE II, HgiA I, Hph I, Mbo II, Sal I, Xma III, Xor II, Nru I, Pvu I, EcoR I, Bcl I, Bgl II, Bal I, Kpn I, Hpa I, Sph I, Ava I, Hind III. The following enzymed cleave the DNA at a single site: Pst I, Xba I, Cla I, Sma I. The restriction patterns deduced for some of these enzymes are given in FIG. 2.

I. Isolation of Deletion Mutants of Phage TG1

Deletion mutants are especially useful for the cloning of DNA. The amount of DNA which can be packaged into a phage particle is finite. A deletion of a portion of the phage DNA allows space for an additional amount of DNA, equal to the size of the deletion, to be inserted into the phage. Deletions also reveal which portions of the phage genome are dispensable and are therefore suitable for the insertion of DNA. Insertion in other regions is more likely to disrupt genes necessary for phage function. Mutants were obtained by the commonly used technique of isolating phage variants resistant to chelating agents (see reference 8). Magnesium ion is necessary for the stability of phage particles. If $Mg^{++}$ is effectively removed by the addition of a chelating agent, in this case ethylenediaminetetraacetate, the number of viable phage decreases rapidly. Phage particles containing shorter DNA molecules due to mutations resulting in the deletion of some of the phage genome are more stable in the absence of $Mg^{++}$ and survive.

To obtain deletion mutants of phage TG1 0.10 ml of 1.0M 2-(N-morpholino)ethanesulfonic acid, which has been adjusted to pH 6.5 with KOH, and 0.10 ml of 0.50M disodium ethylenediaminetetraacetate, which has been adjusted to pH 7 with NaOH, are mixed with 1.0 ml of a phage plate or tube stock. The mixture is incubated at 37° C. for 30 minutes; it is then added to a 250 ml Erlenmeyer flask containing 25 ml of YC broth and 0.10 ml of germlings. Sometimes it is necessary to add 0.50 ml of a solution of 10 mg per ml of $FeCl_3.6H_2O$ in 5 mM HCl in order to obtain growth of the phage. The necessity of this depends on the particular batch of YC broth. The flask is shaken on a 140 r.p.m. shaker (2 inch throw) at 30° C. for 16 hours. The liquid lysate obtained after overnight incubation is filtered through a filter with a pore size of 0.45 microns and the concentration of viable phage determined. If this is greater than $10^7$ pfu per ml, the treatment with ethylenediaminetetraacetate is repeated, as well as the subsequent growth of the phage. The first treatment with ethylenediaminetetraacetate results in about a $10^4$ to $10^5$-fold drop in pfu per ml. Subsequent treatments result in progressively less severe decreases in pfu per ml. The treatments are usually repeated three times. After the final treatment, DNA of phages propagated from single plaques is purified and analyzed by digestion with restriction endonucleases. Many of the cloned phage populations have suffered a deletion of a portion of their DNA. Restriction analysis of such deletion phages reveals the occurrence of at least four types of phage deletion variants. Examples of these are phages TG2, TG3, TG4, and TG5 (see FIG. 3). The phage DNA molecules were examined for the presence or absence of the restriction sites of the enzymes Hind III, Kpn I, Pst I, and Sph I. Phage TG2 has a deletion of 2.0 kbp of DNA which removes the Sph I site at 6.72 kbp, the Kpn I site at 7.93 kbp, and the Hind III site at 7.99 kbp. Phage TG3 has a deletion of 2.5 kbp of DNA which removes the Kpn I site at 7.93 kbp, the Hind III site at 7.99 kbp, and the Pst I site at 8.38 kbp. Phage TG4 has a deletion of 1.8 kbp of DNA which removes the Sph I site at 6.72 kbp. Phage TG5 has a deletion of 2.1 kbp of DNA which removes the Sph I site at 6.72 kbp, the Kpn I site at 7.93 kbp, and the Pst I site at 8.38 kbp. Lysogens of *S. cattleya* NRRL 8057 capable of releasing these phages have been deposited (see Table I) as strain ATCC 39077 (MA5766), releasing phage TG2; strain NRRL 15034 (MA5769), releasing phage TG4, and strain NRRL 15035 (MA5770), releasing phage TG5. It is likely that other types of deletion mutants can be obtained, and that these will be useful. FIG. 3 indicates that portion of the TG1 genome which has been deleted in each of these phages. All of the deletion mutants shown in FIG. 3 are capable of forming lysogens. This may not be true of all deletion mutants which may eventually be obtained. The region of DNA which is deleted in the phages shown in FIG. 3 is not necessary for either the lytic or lysogenic functions of the phage. Two of the deletions remove the single Pst I site of the phage genome. It has been demonstrated without affecting phage functions, and that this site is therefore a useful site for the insertion of DNA which is to be cloned (see Section M). Two of the deletion types leave the Pst I site intact. These DNA molecules are especially useful for the insertion of DNA which is to be cloned. It is probable that sites other than that for Pst I will be found which are also useful for the cloning of DNA.

J. Transfection of Streptomyces cattleya MA4297

Transfection is carried out in the following manner. Germlings are harvested by centrifugation and resuspended at a concentration of about $10^{10}$ cfu per ml with 2.0 ml PMC20. PMC20 is prepared by dissolving 200 g sucrose, 0.25 g $K_2SO_4$, 2.0 g $MgCl_2.6H_2O$ and 2.0 ml of trace elements in water to give a final volume of 1.0 liter; after autoclaving, 10 ml of 2.5M $CaCl_2$ and 10 ml of a solution of 1.0M 2-(N-morpholino)ethanesulfonic acid and 0.5% (w/v) $KH_2PO_4$, adjusted to pH 6.0 with KOH, is added per liter. Trace elements contain 40 mg $ZnCl_2$, 200 mg $FeCl_3.6H_2O$, 10 mg $CuCl_2.2H_2O$, 10 mg $MnCl_2.2H_2O$, 10 mg $Na_2B_4O_7.10H_2O$, and 10 mg of $(NH_4)_6Mo_7O_{24}.4H_2O$ per liter. To the germling suspension is added 2.0 ml of hen egg white lysozyme (2 mg per ml in PMC20). The mixture is incubated at 37° C. for 90 min after which time the protoplasts are collected by centrifugation for 5 minutes at $2500 \times g$. The pellet is resuspended with 4.0 ml of PMC20 and kept on ice. A sample of DNA, for example, 20 $\mu$l containing 0.25 $\mu$g per microliter of vector DNA is mixed with an equal volume of heparin solution (Sigma, sodium salt, 5 mg per ml in 2-fold concentrated PMC20) and 240 $\mu$l of PMC20 is added. A 0.30 ml sample of the protoplast suspension is added, followed by 1.50 ml of 28% (w/v) polyethylene glycol (Sigma, avg. mol. wt. 1000) dissolved in PMC20. This mixture is incubated for 10 min at room temperature. Samples of 0.7 ml are mixed with 10 ml RM soft agar and 0.2 ml of spores of S. cattleya at a concentration of $10^7$ cfu per ml in PMC20 and immediately poured into square petri plates ($100 \times 15$ mm) containing about 60 ml of RM agar. RM contains 200 g sucrose, 0.25 g $K_2SO_4$, 10 g $MgCl_2.6H_2O$, 10 g D-glucose, 0.1 g Difco casamino acids, 3.5 g Difco oatmeal agar, 2.0 ml trace elements, 3 g L-proline, 2 g Difco yeast extract and 1.95 g 2-(N-morpholino)ethanesulfonic acid, mixed thoroughly in water, adjusted to pH 6.0 with KOH, diluted to 1.0 liter, and autoclaved; after autoclaving, 8.0 ml of 2.5M $CaCl_2$ and 10 ml of 0.5% (w/v) $KH_2PO_4$ are added per liter. RM agar is RM solidified with 2.0% (w/v) Difco agar, and RM soft agar is RM containing 0.6% (w/v) molten Difco agar at 46° C. After the soft agar overlay has hardened, the plates are incubated for two days at 28° C. Phage are isolated from zones of bacterial lysis and propagated.

K. Transformation of Escherichia coli K-12 RR-1

E. coli cells competent for the uptake of DNA are prepared in the following manner. Eschericha coli K-12 RR1 (see F. Bolivar, R. L. Lodriquez, M. C. Betlach and H. W. Boyer, 2 Gene, pp. 75–93 (1977)) is grown exponentially in 250 ml medium LB at 37° C. LB contains 10 g Bacto-tryptone, 5 g Bacto-yeast extract, and 5 g NaCl per liter of distilled water. When the cell concentration has reached $2 \times 10^8$ cfu per ml, the culture is cooled to ice temperature for 15 minutes before collecting the cells by centrifugation ($6,000 \times g$ for 5 minutes) at 4° C. The supernatant fluid is discarded, and the cells are resuspended with 125 ml of ice-cold 0.10M $CaCl_2$. The cell suspension is maintained on ice for 15 minutes. The cells are collected again by centrifugation, resuspended with 25 ml of ice-cold 0.10M $CaCl_2$, and kept on ice for an additional 15 minutes. An ice-cold solution (15 ml) containing 40% glycerol (w/v) in 0.10M CaCl, is mixed with the cell suspension, which can be stored at $-70°$ C., or used directly.

DNA (approximately 0.1 to 1.0 $\mu$g in 30 $\mu$l of TE), is mixed with 100 $\mu$l of a solution containing 50 mM NaCl, 5 mM trisodium citrate, and 67 mM $CaCl_2$. The cell suspension (0.20 ml) is added, and the mixture is heated at 37° C. for 2 minutes, then put on ice for 45 minutes to an hour. Medium LB (4.0 ml) is added and the cells incubated for 3 hours at 37° C. with shaking. This period of growth allows for the estabishment of the plasmid and expression of a selectable trait conferred by the transforming DNA. The cells are concentrated by centrifugation and various amounts spread on agar plates containing medium allowing the growth of only those organisms acquiring the trait provided by the added DNA, for instance, LB solidified with 1.5% (w/v) Difco-agar and supplemented with antibiotic, such as kanamycin at a concentration of 50 $\mu$g per ml.

L. Preparation of Plasmid DNA from E. Coli K-12

Plasmid DNA can be isolated from plasmid-containing derivatives of E. coli K-12 by standard procedures as described, for example, by Davis et al., supra, pp. 116–119. Less pure DNA which is nevertheless suitable for transformation, transfection or restriction analysis can be isolated more rapidly as follows. Cells are grown overnight to stationary phase in 5 ml of selective medium, usually LB supplemented with an antibiotic. The cells are harvested by centrifugation ($3,000 \times g$ for 5 minutes and resuspended with 0.45 ml of a solution containing 8% (w/v) sucrose, 5% (w/v) Triton X-100, 50 mM disodium ethylenediaminetetraacetate, and 50 mM tris(hydroxymethyl)aminomethane, the whole adjusted to pH 8.0 with KOH. Lysozyme (25 $\mu$l of a freshly prepared solution at 10 mg per ml in TE) is added. The mixture is incubated in boiling water for 60 sec and centrifuged immediately thereafter at room temperature ($12,000 \times g$ for 10 minutes). A portion of 100 $\mu$l of the supernatant fluid is withdrawn and mixed with 100 $\mu$l of isopropanol. After 30 minutes incubation at $-20°$ C. the precipitate of DNA is recovered by centrifugation ($12,000 \times g$ for 10 min.), dissolved with 100 $\mu$l TE, and stored at 4° C. Portions of from 5 to 20 $\mu$l are sufficient for restriction analysis, transfection, or transformation.

M. Insertion of Plasmid pACYC177 into Phage TG2 DNA

This experiment demonstrates the feasibility of cloning foreign DNA into this vector.

The plasmid pACYC177 is described by A. C. Y. Chang and S. N. Cohen, J. Bacteriol. 134 (1978) 1141–1156. It is derived from E. coli and is about 3.9 kilobasepairs in size. It provides resistance to ampicillin and to kanamycin and has a single Pst I site within the DNA sequence coding for resistance to ampicillin. Covalently closed pACYC177 plasmid DNA and phage TG2 DNA were cleaved separately by incubation at 37° C. for 8 hr in 0.25 ml reaction mixtures consisting of 50 $\mu$g of DNA in 0.20 ml of TE mixed with 0.05 ml of 5XKC (0.1M tris(hydroxymethyl)aminomethane, 50 mM $MgCl_2$, 0.1M KCl, adjusted to pH 7.7 with HCl) and 15 $\mu$l of Pst I endonuclease (150 units, Bethesda Research Laboratories). An additional 100 units of endonuclease was added to the reaction mixture containing phage DNA after four hours of incubation. Each mixture was heated 10 min at 70° C., after which 1.0 $\mu$l of diethylpyrocarbonate was added and an additional incubation for 1 hr at 37° C. was employed to inactivate the endonuclease. The DNA was precipitated by the addition of ethanol, as described previously, and redissolved with 0.20 ml of TE. Samples of each cleaved DNA (75 μl) were mixed with each other plus 75 μl of TE, 28 μl of LM (0.66M tris(hydroxymethyl)aminomethane, 66 mM $MgCl_2$, adjusted to pH 7.5 with HCl), 25 μl of 4.0 mM adenosine-5'-triphosphate (disodium salt), 25 μl of 0.10M dithiothreitol and 3 μl of T4 DNA ligase (6 units, Bethesda Research Laboratories). The mixture was incubated for 24 hr at 3.5° C. The DNA was precipitated with ethanol, as described previously, and redissolved with 75 μl of TE. Portions of this DNA preparation were used to transfect protoplasts of S. cattleya as described in Section J. Phage were isolated, and their DNA examined by restriction analysis. Phage were obtained whose DNA differed from that of the parent phage by the insertion, at the single Pst I site, of DNA having the size and restriction properties of plasmid pACYC177, which could be excised in linear form by digestion with Pst I. Two phages, TG6 and TG7, having pACYC177 inserted in opposite orientations, as indicated in FIG. 4, were obtained. DNA of these phages was used to transform E. coli K-12 RR1 as described in Section K. Transformants were selected on petri plates containing LB solidified with 1.5% (w/v) Difco-agar and supplemented with kanamycin at 50 μg per ml.

The plates were incubated overnight at 37° C. A large number of colonies of kanamycin resistant bacteria were obtained from cells exposed to DNA of phages TG6 and TG7. Such bacteria were repurified, and have been deposited as strain ATCC 39079 (MB4540) containing plasmid pTG6 derived from phage TG6, and as strain ATCC 39082 (MB4543) containing plasmid pTG7 derived from phage TG7. Plasmid DNA was isolated from these strains as described in Section L and was examined by restriction analysis with Hind III. The plasmids were identical to the DNA of the corresponding vegetative phages, TG6 and TG7, except that the cohesive ends were joined. Furthermore, the undigested DNA preparations were used to transfect protoplasts of Streptomyces cattleya MA4297 in a manner similar to that described in Section J and gave rise to phage indistinguishable by similar criteria from phages TG6 and TG7.

N. Isolation of Deletion Mutants of the Hybrid Phages

The insertion of the plasmid pACYC177 into deletion phage TG2 results in a page whose genome (nucleic acid) is about 4.7% longer than that found in the original isolate TG1. The extra length of DNA packaged in this phage renders it more sensitive to chelating agents than the original isolate. This trait can be utilized for the isolation of deletion mutants in the following manner. It should be noted that the insertion of any DNA into any derivative of phage TG1 which results in a genome size greater than that of the original isolate will have similar properties.

To isolate deletion mutants of phages TG6 and TG7 10 μl of a tube stock prepared from a single plaque is mixed with 0.10 ml of YC broth which lacks divalent cation additions and has been supplemented with 25 mM sodium pyrophosphate and adjusted to pH 6.0 with NaOH. After 30 minutes incubation at 35° C., at which time the number of surviving phage is about $10^{-3}$ of the initial concentration, 0.20 ml of germlings in YC broth is added. After 10 to 20 minutes at room temperature, 4.0 ml of YC soft agar is added, and the mixture is poured over a YC agar plate, and incubated overnight at 30° C. A phage plate stock is prepared. The treatment of the phage with pyrophosphate is repeated two more times in succession.

The fraction of surving phage is substantially greater after the second and third treatments. DNA of single plaque isolates from such pyrophosphate resistant phage preparations is usually deleted in the region of the inserted plasmid. The deletions are from 4 to 6 kbp in average size. To select mutants with deletions other than of the inserted plasmid, DNA is isolated from phage tube stocks prepared directly from a 0.10 ml sample of the pyrophosphate resistant phage plate stock. Such a stock constitutes a mixed population, some members of which are mutant phages with the desired deletions. The DNA is used to transform E. coli K-12 RR1 to kanamycin resistance. The plasmid DNA of such transformants must retain the replication functions and the kanamycin resistance gene of the inserted pACYC177 plasmid. Derivatives with inserted DNA conferring alternative selectable traits can be utilized in a similar manner. If the trait is expressed in S. cattleya rather than in E. coli, the relevant deletion mutants can be obtained by direct infection of S. cattleya germlings with the mixed pyrophosphate resistant phage population. After adsorption of the phage, the germlings are grown for 2 to 4 hours to allow establishment of the vector molecule and expression of the selectable trait before being transferred to the selective medium.

Vector DNA is isolated from the transformed cells (or as the case may be from phage released by lysogens) and analyzed for the presence of deletions. Kanamycin resistant transformants obtained with DNA from pyrophosphate resistant populations of phages TG6 and TG7, contained plasmids with deletions located between the left end of the vegetative phage DNA restriction map (as presented in FIG. 4) and the kanamycin resistance gene of the inserted plasmid. The location relative to the restriction maps of phage TG6 and TG7 and sizes of these deletions are indicated in FIG. 4. The plasmids were analyzed with the restriction enzymes Hind III, Sph I, Pst I, Sma I and BamH I. The following plasmids were derived from TG6: pTG8 has a deletion of 3.1 kbp of DNA which removes the Pst I site at 6.38 kbp and the BamH I site at 7.27 kbp; pTG9 has a deletion of 4.7 kbp of DNA which removes the Sph I site at 4.75 kbp, the Pst I site at 6.38 kbp, and the BamH I site at 7.27 kbp; pTG10 has a deletion of 3.0 kbp of DNA which removes the Hind III site at 1.66 kbp; pTG11 has a deletion of 2.0 kbp of DNA which removes the Pst I site at 6.38 kbp and the BamH I site at 7.27 kbp; pTG12 has a deletion of 6.0 kbp of DNA which removes the Sph I site at 4.75 kbp, the Pst I site at 6.38 kbp, and the BamH I site at 7.27 kbp; pTG13 has a deletion of 2.8 kbp of DNA which removes the Pst I site at 6.38 kbp and the BamH I site at 7.27 kbp; and pTG14 has a deletion of 4.1 kbp of DNA which removes the Sph I site at 4.75 kbp. The following plasmids were derived from TG7: pTG15 has a deletion of 3.1 kbp which removes the Sph I site at 4.75 kbp; and pTG16 has a deletion of 4.6 kbp which removes the Sph I site at 4.75 kbp. Representative strains containing some of these plasmid derivatives were deposited as strain ATCC 39080 (MB4541) containing plasmid pTG12; strain ATCC 39081 (MB4542) containing plasmid pTG16; strain NRRL B-15027 (MB4544) containing plasmid pTG8; strain NRRL B-

15028 (MB4545) containing plasmid pTG9; strain NRRL B-15029 (MB4546) containing plasmid pTG10; strain NRRL B-15030 (MB4547) containing plasmid pTG11; strain NRRL B-15031 (MB4548) containing plasmid pTG13; strain NRRL B15032 (MB4549) containing plasmid pTG14; strain NRRL B-15033 (MB4550) containing plasmid pTG15.

These plasmids were used to transfect protoplasts of S. cattleya and gave rise to phages whose DNA was identical to the corresponding plasmid DNA, except that the cohesive ends could be separated. Plasmid pTG8 gave phage TG8; pTG9 gave phage TG9, and so forth.

EXAMPLE 2

Cloning of Thienamycin Genes

This example shows how a derivtive of the TG1 vector can be used for the identification and cloning of thienamycin genes. This experiment can be carried out in numerous ways and the method described here is meant only to be illustrative, and not in any way limitative, of how TG1 vector and its derivaties can be used to accomplish this goal.

A. Construction of TG1 Derivative Carrying a Gene for Resistance to Thiostrepton.

The construction of a TG1 derivative carrying a gene for resistance to a drug allows the direct selection of lysogens. This is useful for screening hybrid vector clones for thienamycin genes (see Section B of this Example). A gene conferring resistance to the antibiotic thiostrepton in Streptomyces has been cloned (see Thompson, C. J. Ward, J. M. and Hopwood, D. A.: DNA cloning in Streptomyces: resistance genes from antibiotic-producing species. *Nature* 286 (1980) 525–527). Plasmid DNA carrying this gene is isolated and cleaved with BamH I. The fragment (2.0 kbp) carrying the thiostrepton resistance gene is purified by agarose gel electrophoresis. The purified fragment is partially digested with Bcl I. The fragment has Bcl I sites on both sides of the drug resistance gene. The partially cleaved DNA and DNA of vector TG15 which has been cleaved with BamH I are mixed and ligated. The ligated DNA is used to transfect protoplasts of Steptomyces cattleya as described in Example 1, Section J, except that after treatment with polyethylene glycol the protoplasts are mixed with 10 ml of RM and spores and incubated overnight at 30° C. in a 250 ml Erlenmeyer flask with slow swirling. The cells are diluted to various degrees and spread onto petri plates containing YC agar supplemented with thiostrepton at a final concentration of 5 and 10 microgram per ml. Colonies result from the growth of thiostrepton resistant lysogens. DNA of phages from these lysogens is analyzed for the presence of BamH I sites.

Hybrid vectors are selected which have a single BamH I site and no BamH I site. Since ends produced by digestion with Bcl I can be ligated with ends produced by digestion with BamH I, but the new junction does not regenerate a site for either enzyme, the insertion of a fragment produced by cleavage with BamH I at one end and Bcl I at the other end gives a vector with a single BamH I site; the insertion of a fragment produced by cleavage with Bcl I at both ends gives a vector with no BamH I site. The insert carrying the thiostrepton resistance gene with a BamH I site at one end is about 1.5 kbp in length. The insert carrying the thiostrepton resistance gene with no BamH I site is 1.1 kbp in length.

A deletion of phage and pACYC177 DNA to the left of the thiostrepton gene is obtained essentially as previously described (see Example 1, Sections I and N). The desired deletion removes 4 to 4.5 kbp of DNA and the Pst I site at the left end of the pACYC177 DNA. It is selected by treating the phage with chelating agent and screening lysogens resistant to thiostrepton for the release of phage with DNA having the desired deletion.

A BamH I site can be introduced into the vector without a BamH I site in the following manner. DNA of plasmid pBR322 is digested with Rsa I and Sph I. The 0.4 kbp fragment produced by this digestion is tailed with 10 to 15 deoxycytidine nucleotide residues as described by Nelson and Brutlag (see T. Nelson and D. Brutlag. Addition of homopolymers to the 3'-ends of duplex DNA with terminal transferase, in vol. 68 (1979) of *Methods In Enzymology*, S. P. Coldwick and N. O. Kaplan (eds.), pp. 41–50). DNA of the vector lacking the BamH I site and deleted of a portion of the phage and plasmid DNA to the left of the inserted thiostrpton resistance gene is cleaved with Pst I. Only a single Pst I site, to the right of the inserted gene, remains in this vector. The cleaved vector DNA is tailed with 10 to 15 deoxyguanosine nucleotide residues (see Nelson and Brutlag, supra). The tailed fragment and the tailed vector are mixed and used to transfect protoplasts of S. cattleya. DNA of the resulting phages is examined for the insertion of the fragment from pBR322. This vector has the advantage in the cloning of random fragments produced by partial digestion with Sau3A I (see Section B) of having Pst I sites and an Sph I site adjacent to the cloned fragments. The trailing of DNA cleaved with Pst I with deoxyguanosine results in the regeneration of the Pst I site in the final hybrid molecule, while the tailing of DNA cleaved with Sph I with deoxycytidine results in the regeneration of the Sph I site. These extra sites can be advantageous for subsequent excision of cloned fragments.

B. Isolation and Identification of Thienamycin Genes

Chromosomal DNA of Streptomyces cattleya is partially digested with Sau3A I. The digestion products are fractionated by agarose gel electrophoresis. Fragments in the range of 3 to 10 kbp in length are extracted from the gel (see Davis et al., supra). These fragments are mixed with the derivtive of vector TG15 which has been cleaved with BamH I. The construction of this derivative is described above. The DNA is ligated and used to transfect protoplasts of S. cattleya and lysogens resistant to thiostrepton are isolated as described in Section A of this example. Many of the vectors in these lysogens carry inserts of Streptomyces cattleya chromosomal DNA. These are screened for the presence of inserts capable of complementing mutants of S. cattleya blocked in the synthesis of thienamycin in the following manner. Phage stocks are prepared from mixtures of the lysogens and are used to infect the various thienamycin mutants in liquid culture. After a few hours of incubation with the phage the cells are spread onto YC agar plates supplemented with thiostrepton. Colonies with cells harboring hybrid vectors carrying a gene capable of complementing the mutation present in the host are detected by flooding the plate with a soft agar overlay inoculated with a thienamycin sensitive organism (see Kahan, J. S., Kahan, F. M., Goegelman, R., Currie, S. A., Jackson, M., Stapley, E. O., Miller, T. W., Miller, A. K., Hendlin, D., Mochales, S., Hernandez, S., Woodruff, H. B. and Birnbaum, J.: Thienamycin, a new beta-lactam antibiotic. I. Discovery, taxonomy, isolation and physical properties. *J. Antibiot.* 32 (1979) 1–12). A colony of an organism carrying such a hybrid vector is at the center of a large circular zone of lysis of the thienamycin sensitive organism. The presence of a hybrid vector is confirmed by analysis of the DNA from phage produced by the lysogen. The presence of a thienamycin gene is confirmed by reinfection of the mutant with the hybrid phage. All lysogens obtained with the new hybrid phage should acquire the ability to synthesize thienamycin.

EXAMPLE 3

Cloning Hepatitis B Surface Antigen Into *S. cattleya*

Hepatitis B surface antigen can be cloned into *S. cattleya* by insertion of the bulk of the C-terminal portion of the hepatitis B surface antigen gene into a gene expressed in *S. cattleya*. If the surface antigen insert is in the correct orientation and translational reading frame, a fusion protein having the antigenic properties of the hepatitis B surface antigen will be produced (see J. C. Edman et al., *Nature* 291 (1981) pp. 503–506). In the present example the hepatitis B surface antigen is inserted into a gene conferring resistance to neomycin. The goal of having the hepatitis B surface antigen expressed in *S. cattleya* can be accomplished in numerous ways. The method described here is meant only to be illustrative, and not in any way limitative, of how TG1 vector and its derivatives can be used to accomplish this goal.

A. Construction of a Derivative of the TG1 Vector Carrying a Gene for Resistance to Neomycin A gene conferring resistance to the antibiotic neomycin in Streptomyces has been cloned (see Thompson et al., supra). This gene codes for neomycin phosphotransferase. Plasmid DNA carrying this gene is isolated and cleaved with Sst II. The fragment (1.0 kbp in length) carrying the neomycin resistance gene is purified by agarose gel electrophoresis. The fragment is mixed with DNA of vector TG8 which has been cleaved with Sst II. Vector TG8 has a unique Sst II site located between the Sma I site and Pst I sites in the pACYC177 portion of its DNA. The DNA is ligated and used to transfect protoplasts of *S. cattleya*. Lysogens resistant to neomycin are isolated (in a manner similar to that described in Example 2, Section A) on YC agar plates supplemented with 10 to 20 microgram per ml of neomycin.

B. Construction of a Derivative of TG1 Expressing a Neomycin Phosphotransferase-Hepatitis B Surface Antigen Fusion Protein DNa of the phage with the neomycin fragment inserted at the Sst II site is cleaved with BamH I. The vector has a single BamH I site which is located near the middle of the gene coding for resistance to neomycin. The vector is tailed with approximately 10 to 15 deoxyguanosine nucleotide residues (see Nelson and Brutlag, supra). Cloned hepatitis B viral DNA is digested with Hinc II and a 744-Base pair fragment containing part of the hepatitis B surface antigen (the 22 amino terminal amino acids are missing) is isolated by polyacrylamide gel electrophoresis (see J. C. Edman, R. H. Hallewell, P. Valenzuela, H. M. Goodman and W. J. Rutter. Synthesis of hepatitis B surface and core antigens in *E. coli*, vol. 291 (1981) *Nature*, pp. 503–506). This fragment is tailed with approximately 10 to 15 deoxycytidine nucleotide residues (see Nelson and Brutlag, supra). The fragment is then hybridized with the tailed vector, and the mixture used to transfect protoplasts of *S. cattleya*. Phage are isolated from the resulting plaques, and their DNA examined for the insertion of the hepatitis B surface antigen fragment by restriction analysis. Lysogens are isolated and examined for the production of the expected neomycin phosphotransferase-hapatis B surface antigen fusion protein (linked by a short run of glycine residues resulting from the deoxyguanosine tail of the amino terminal end of the neomycin gene) by immunoprecipitation of $^{35}$S-cysteine-labelled protein extracts (see Edman et al., supra). Since the inserted hepatitis B surface antigen fragment must be in the correct orientation and correct reading frame, only about one of six of the hybrid clones will produce the fusion protein.

What is claimed is:

1. An isolated vector consisting essentially of TG1 prophage, or its respective genome.

2. An isolated vector according to claim 1 including additional foreign DNA.

3. A biologically pure culture of a microorganism containing a vector according to claim 1 wherein said microorganism is one which can act as a host for said vector with respect to lytic growth, transformation, or lysogeny.

4. A biologically pure culture of a microorganism according to claim 3 wherein the microorganism is selected from the group consisting essentially of *Streptomyces cattleya, Streptomyces avermitilis, Streptomyces viridochromogenes,* and *Streptomyces garyphlus*, and wherein said microorganism is one which can act as a host for said vector with respect to lytic growth, transformation, or lysogeny.

5. A biologically pure culture of a microorganism containing a vector according to claim 2 wherein said microorganism is one which can act as a host for said vector with respect to lytic growth, transformation, or lysogeny.

6. An isolated vector consisting essentially of a member selected from the group consisting essentially of: (A) a bacteriophage selected from the group consisting of TG2 through TG16 inclusive, or its respective genome; (B) a prophage selected from the group consisting of TG2 through TG8 inclusive, TG11, and TG13, or its respective genome; and (C) a plasmid selected from the group consisting of TG6 through TG16 inclusive.

7. An isolated vector according to claim 6 including additional foreign DNA.

8. A biologically pure culture of a microorganism containing a vector according to claim 6 wherein said microorganism is one which can act as a host for said vector with respect to lytic growth, transformation, or lysogeny.

9. A biologically pure culture of a microorganism according to claim 6 wherein the microorganism is selected from the group consisting essentially of *Streptomyces cattleya, Streptomyces avermitilis, Streptomyces viridochromogenes,* and *Streptomyces grayphlus*, and wherein said microorganism is one which can act as a host for said vector with respect to lytic growth, transformation, or lysogeny.

10. A biologically pure culture of a microorganism containing a vector according to claim 7 wherein said microorganism is one which can act as a host for said vector with respect to lytic growth, transformation, or lysogeny.

11. A method for preparing a derivative of an isolated vector consisting essentially of TG1 bacteriophage, its genome, TG1 prophage, or its respective genome, comprising the separate steps of adding and deleting DNA from said vector, said steps being carried out once or successively, solely to the exclusion of the other, or together in any order, followed by a step of recovering said derivative.

12. A method according to claim 11 for the deletion of DNA from said isolated vector which comprises treating said vector with a chelating agent which has greater affinity for divalent cations than said vector.

13. A method according to claim 12 wherein the chelating agent is ethylenediaminetetraacetate or pyrophosphate.

14. A method according to claim 11 for the addition of DNA to said isolated vector which comprises cleaving the DNA of said vector and incorporating additional DNA.

15. A method according to claim 11 for the deletion of DNA from said isolated vector which comprises cleaving the DNA of said vector.

16. A method according to claim 11 for the addition of DNA to said isolated vector which comprises treating said vector with a restriction endonuclease.

17. A method according to claim 16 wherein the restriction endonuclease is selected from the group consisting of Bam H I, Cla I, Nae I, Nar I, Nde I, Pst I, Pvu II, Sac I, Sac II, Sma I, Sst I, Sst II, Xbu, and Xho I.

18. A method for preparing a derivative of an isolated vector consisting essentially of a member selected from the group consisting essentially of: (A) a bacteriophage selected from the group consisting of TG2 through TG16 inclusive, or its respective genome; (B) a prophage selected from the group consisting of TG2 through TG8 inclusive, TG11, and TG13, or its respective genome; and (C) a plasmid selected from the group consisting of TG6 through TG16 inclusive comprising the separate steps of adding and deleting DNA from said vector, said steps being carried out once or successively, solely to the exclusion of the other, or together in any order, followed by a step of recovering said derivative.

19. A method according to claim 18 for the deletion of DNA from isolated vector which comprises treating said vector with a chelating agent which has greater affinity for divalent cations than said vector.

20. A method according to claim 19 wherein the chelating agent is ethylenediaminetetraacetate or pyrophosphate.

21. A method according to claim 18 for the addition of DNA to said isolated vector which comprises cleaving the DNA of said vector and incorporating additional DNA.

22. A method according to claim 18 for the deletion of DNA from said isolated vector which comprises cleaving the DNA of said vector.

23. A method according to claim 18 for the addition of DNA to said isolated vector which comprises treating said vector with a restriction endonuclease.

24. A method according to claim 23 wherein the restriction endonuclease is selected from the group consisting of Bam H I, Cla I, Nae I, Nar I, Nde I, Pst I, Pvu II, Sac I, Sac II, Sma I, Sst I, Sst II, Xbu, and Xho I.

25. An isolated vector prepared by the method of claim 11.

26. An isolated vector prepared by the method of claim 18.

* * * * *